(12) United States Patent
Tsubota et al.

(10) Patent No.: US 8,513,609 B2
(45) Date of Patent: Aug. 20, 2013

(54) MANAGEMENT DEVICE, STORAGE MEDIUM STORED WITH PROGRAM AND IMAGING DEVICE

(75) Inventors: Keiji Tsubota, Kanagawa (JP); Yutaka Yoshida, Kanagawa (JP); Takeshi Kamiya, Kanagawa (JP); Naoyuki Nishino, Kanagawa (JP); Yasunori Ohta, Kanagawa (JP); Keiichiro Sato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 954 days.

(21) Appl. No.: 12/546,709

(22) Filed: Aug. 25, 2009

(65) Prior Publication Data

US 2010/0061616 A1    Mar. 11, 2010

(30) Foreign Application Priority Data

Sep. 8, 2008  (JP) ................ 2008-230215
Jul. 30, 2009  (JP) ................ 2009-177972

(51) Int. Cl.
  *G01J 5/02*  (2006.01)
  *G06T 7/00*  (2006.01)
(52) U.S. Cl.
  USPC .......................... 250/349; 382/132
(58) Field of Classification Search
  USPC ............... 250/349, 559.4; 378/37; 382/132, 382/195
  See application file for complete search history.

(56) References Cited

U.S. PATENT DOCUMENTS

2010/0054401 A1*  3/2010  Blendl et al. .............. 378/37

FOREIGN PATENT DOCUMENTS

| JP | 3-251332 A | 11/1991 |
| JP | 20000253318 A | 9/2000 |
| JP | 2000-312445 A | 11/2000 |
| JP | 2003-1342 A | 1/2003 |
| JP | 2005-095635 A | 4/2005 |
| JP | 2008-099808 A | 5/2008 |

OTHER PUBLICATIONS

Partial English language translation of the following: Office action dated Mar. 26, 2013 from the Japanese Patent Office in a Japanese patent application corresponding to the instant patent application.
Partial English language translation of the following: Office action dated Jun. 18, 2013 from the JPO in a Japanese patent application corresponding to the instant patent application.

* cited by examiner

*Primary Examiner* — David Porta
*Assistant Examiner* — Faye Boosalis
(74) *Attorney, Agent, or Firm* — SOLARIS Intellectual Property Group, PLLC

(57) ABSTRACT

A management device that includes an acquiring component and a numericalizetion component is provided. The acquiring component acquires correlation information that correlates with a degree of deterioration of a radiation detection component from plurality of imaging devices, each of the plurality of imaging devices comprising a radiation detection component that detects radiation that has passed through respective investigation subjects, and each of the plurality of imaging devices performing image capture by generating image data representing a radiographic image according to the amount of radiation detected by the radiation detection component, and storing the image data in a predetermined storage region. The numericalization component numericalizes the degree of deterioration of each of the respective radiation detection components of the plurality of imaging devices based on the correlation information acquired by the acquiring component.

11 Claims, 15 Drawing Sheets

FIG.8

DEGREE OF DETERIORATION OF ID NUMBER XXXXX = 135

DEGREE OF DETERIORATION OF ID NUMBER YYYYY = 120

DEGREE OF DETERIORATION OF ID NUMBER ZZZZZ = 190

USE OF ELECTRONIC CASSETTE WITH
ID NUMBER ZZZZZZ IS RECOMMENDED

92

MANAGEMENT DEVICE, STORAGE MEDIUM STORED WITH PROGRAM AND IMAGING DEVICE

CROSS-REFERENCE TO RELATED APPLICATION

This application claims priority under 35 USC 119 from Japanese Patent Applications No. 2008-230215 filed on Sep. 8, 2008 and No. 2009-177972 filed on Jul. 30, 2009, the disclosure of which are incorporated by reference herein.

BACKGROUND OF THE INVENTION

1. Field of the Invention

The present invention relates to a management device and to a storage medium stored with a program. The present invention in particular relates to a management device that manages a imaging device that images by detecting radiation passing through an investigation subject, generating image data representing a radiographic image according to the amount of radiation detected, and storing the image data in a predetermined storage region, a storage medium stored with a program for the same and an imaging device.

2. Description of the Related Art

Recently FPD's (flat panel detectors) that can directly convert radiation into digital data have been put into practice, the FPD's having a radiation sensitive layer disposed on a TFT (thin film transistor) active matrix substrate. Portable imaging devices have also recently been put into practice using such FPD's or the like, the portable imaging devices imaging by generating image data representing a radiographic image according to the amount of radiation irradiated thereon, and storing the generated image data.

However, an issue with such types of portable imaging devices is that the properties of the FPD deteriorate with each successive image capture.

Technology is described in Japanese Patent Application Laid-Open (JP-A) No. 2008-99808 that selects a portable imaging device from plural portable imaging devices, based on quality data, such that the portable imaging devices are used equally.

However, the technology in JP-A No. 2008-99808 operates in a manner that is inconvenient for a user who desires to concentrate usage on particular portable imaging device(s) from plural portable imaging devices.

SUMMARY OF THE INVENTION

The present invention is one that addresses the above issues, and provides a management device capable of supporting concentrated use of particular imaging device(s) from plural imaging devices, a storage medium stored with a program of the same, and an imaging device.

According to a first aspect of the invention, there is provided a management device comprising: an acquiring component that acquires correlation information that correlates with a degree of deterioration of a radiation detection component from plurality of imaging devices, each of the plurality of imaging devices comprising a radiation detection component that detects radiation that has passed through respective investigation subjects, and each of the plurality of imaging devices performing image capture by generating image data representing a radiographic image according to the amount of radiation detected by the radiation detection component, and storing the image data in a predetermined storage region; and a numericalization component that numericalizes the degree of deterioration of each of the respective radiation detection components of the plurality of imaging devices based on the correlation information acquired by the acquiring component.

According to a second aspect of the invention, there is provided a storage medium readable by a computer. The storage medium stores a program of instructions executable by the computer to perform a function of managing imaging devices. The function includes: numericalizing the degree of deterioration of each of respective radiation detection components of a plurality of imaging devices, each of the plurality of imaging devices comprising one of the radiation detection components that detects radiation that has passed through respective investigation subjects, and each of the plurality of imaging devices performing image capture by generating image data representing a radiographic image according to the amount of radiation detected by the radiation detection component, and storing the image data in a predetermined storage region.

According to a third aspect of the invention, there is provided an imaging device comprising: a radiation detection component that detects radiation that has passed through a respective investigation subject; a generation component that generates image data representing a radiographic image according to the amount of radiation that has been detected by the radiation detection component; a storage component that stores the image data that has been generated by the generation component; and a numericalization component that numericalizes a degree of deterioration of the radiation detection component based on correlation information that correlates with the degree of deterioration of the radiation detection component.

BRIEF DESCRIPTION OF THE DRAWINGS

Exemplary embodiments of the present invention will be described in detail based on the following figures, wherein:

FIG. 8 is a view showing an example of plural sets of ID numbers and degrees of deterioration as displayed on a display according to the first exemplary embodiment;

FIG. 9 is a view showing an example of a recommendation message as displayed on a display according to the first exemplary embodiment;

DETAILED DESCRIPTION OF THE INVENTION

The best mode of the present invention will be explained in detail below with reference to the drawings.

First Exemplary Embodiment

Figure 1:
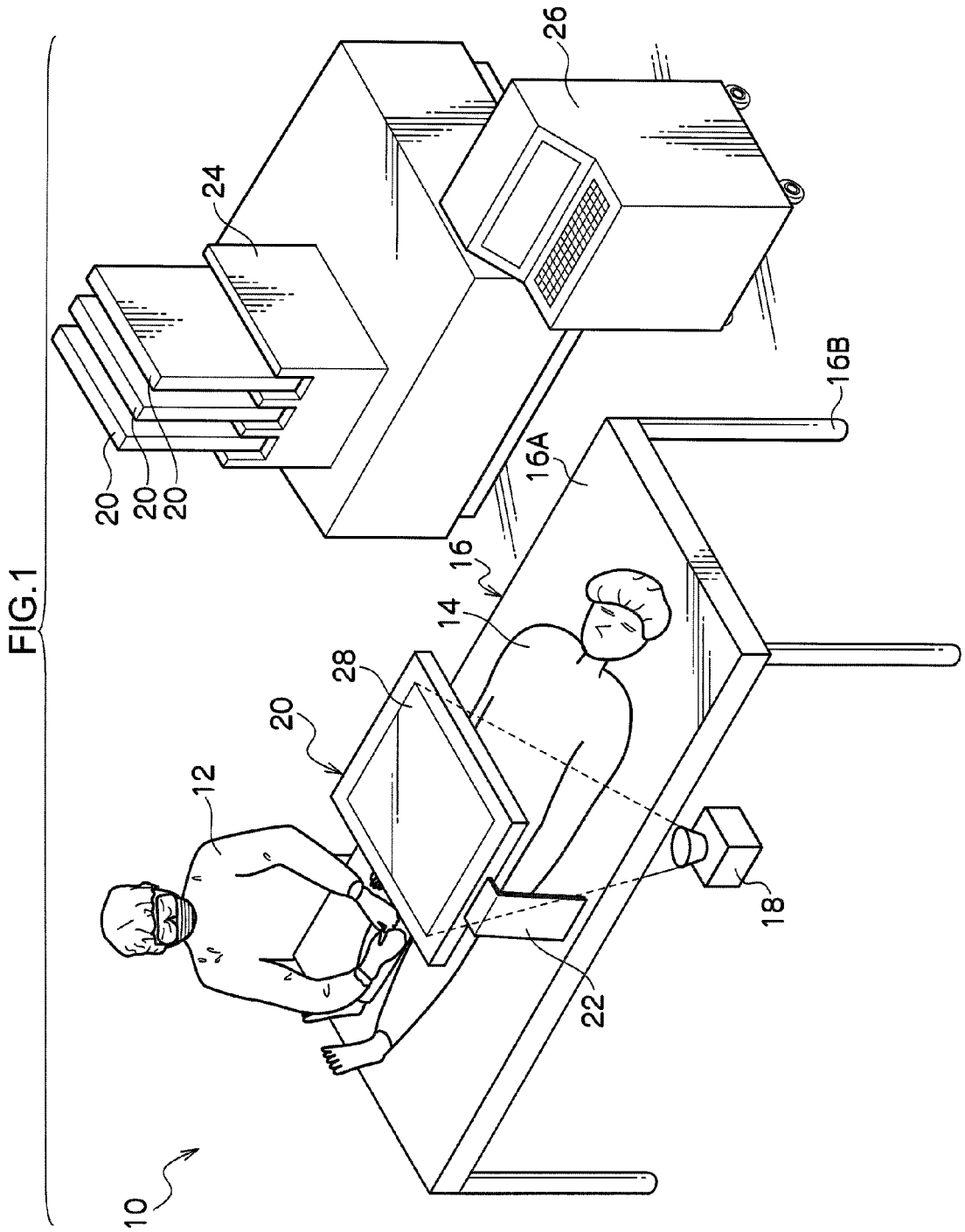
FIG. 1 shows a layout in an operating theatre disposed with an imaging system according to an exemplary embodiment.

Explanation will first be given of the configuration of a radiographic imaging system 10 according to a first exemplary embodiment (referred to below as imaging system 10). FIG. 1 shows a layout in an operating theatre in which the imaging system 10 is disposed, as an example of a layout for disposing the imaging system 10 according to the first exemplary embodiment.

The imaging system 10 is a system for capturing radiographic images by operation by a doctor 12 or radiographer. The imaging system 10 includes: an operating table 16 on which a patient 14 lies; a radiation irradiating device 18 that irradiates the patient 14 with X-ray radiation of a radiation amount according to the imaging conditions; a portable imaging device 20 (referred to below as an electronic cassette 20) that images by detecting X-rays that have passed through the patient 14, generating radiographic image data representing a radiographic image according to the amount of radiation detected (referred to below simply a "image data"), and storing the image data in a predetermined storage region; a support member 22 that supports the electronic cassette 20 in a cantilevered manner from one side of the table 16 on which the patient 14 is lying; a cassette stand 24 in which plural of the electronic cassettes 20 are separated and accommodated in an upright state; and a consol 26 that controls the radiation irradiating device 18, the electronic cassette 20 and the cassette stand 24.

The operating table 16 is configured from a material that permits X-rays to pass through, and has a substantially rectangular flat shaped table top 16A, and legs 16B for supporting the table top 16A, provided at the four corners of the table top 16A.

The radiation irradiating device 18 is disposed at the rear side of the table top 16A, so as to irradiate X-rays onto the patient 14 lying on the table top 16A from the rear side of the table top 16A (the opposite side to that on which the patient 14 is lying).

The electronic cassette 20 is provided on the rear face thereof with a display 28 for displaying captured radiographic images, and in the state in which the display 28 is facing upwards, a later described radiation detection component 36 is disposed at the table top 16A side of the electronic cassette 20, so as to detect X-rays irradiated from the radiation irradiating device 18 and passing through the table top 16A and the patient 14.

The support member 22 is provided at the side of the face of the table top 16A on which the patient 14 is lying. The support member 22 is bent into substantially an L-shape, and the base end thereof is fixed to the table top 16A, with the electronic cassette 20 detachably mounted to the leading end thereof.

Figure 2:
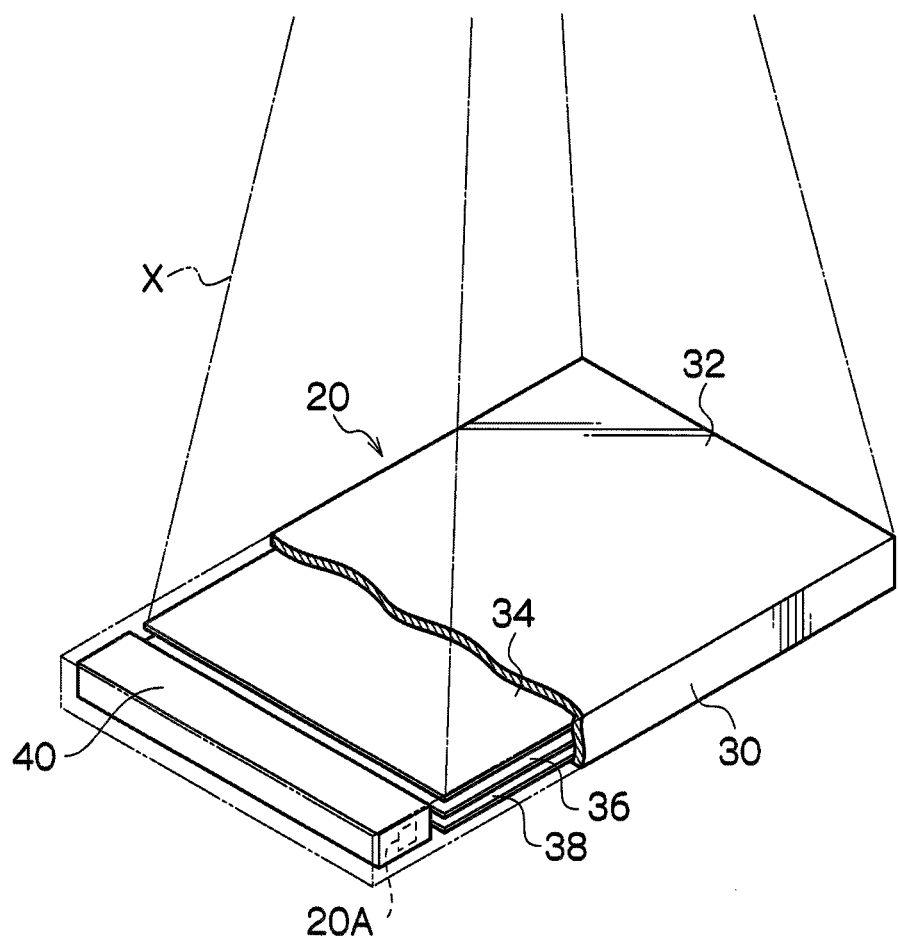
FIG. 2 is a perspective view showing the internal configuration of an electronic cassette according to an exemplary embodiment.

The internal configuration of the electronic cassette 20 according to the first exemplary embodiment is shown in FIG. 2.

As shown in FIG. 2, the electronic cassette 20 is configured with a case 30, made from a material permitting X-rays to pass through in a substantially rectangular flat plate shape. There is a concern that blood fluids and germs etc. adhere to the electronic cassette 20 as it is being used in the operating theatre. In order to address this issue the case 30 is of a waterproof, tightly sealed construction, and therefore a single one of the electronic cassettes 20 can be reused successively by sterilization cleaning as required. A connection terminal 20A is provided in one of the side faces of the case 30 so that a communications cable can be connected. Within the case 30 are provided, in sequence from an irradiation face 32 of the case 30 on which X-rays are irradiated: a grid 34, for removing scattered X-rays; a radiation detection component 36 for detecting X-rays irradiated from the irradiation face 32 that have passed through the patient 14, and for outputting image data representing a radiographic image according to the amount of radiation detected; and a lead plate 38, for absorbing back scattering X-rays.

A case 40, housing electronic circuits including a microcomputer and a rechargeable battery that can be recharged, is internally disposed at one end of the case 30. The radiation detection component 36 and the electronic circuit are operated by electrical power supplied from the rechargeable battery housed in the case 40. In order to avoid damage to the various circuits housed within the case 40, caused by irradiation with X-rays, shielding material for shielding from radiation, such as a lead plate or the like, is preferably disposed at the irradiation face 32 side of the case 40.

Figure 3:
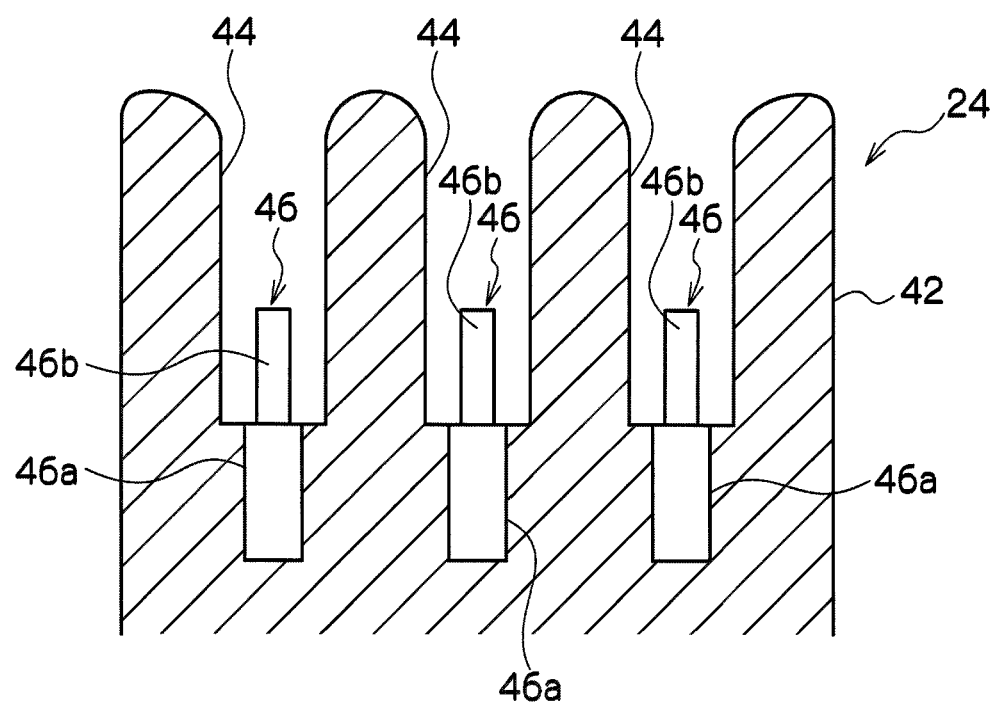
FIG. 3 is a cross-section showing the internal configuration at an end of a cassette stand according to an exemplary embodiment.

FIG. 3 is a view showing the internal configuration of an end of a cassette stand 24 according to the first exemplary embodiment;

As shown in FIG. 3, valley shaped indented insertion grooves 44 (three in the present exemplary embodiment) are formed in the top face of a casing 42 of a cassette stand 24. There is a substantially rectangular shaped opening formed in each of the insertion grooves 44, with the size of the opening of a sufficient size for the case 30 of the electronic cassette 20 to be insertable therein.

An electrical actuator 46 is provided at the bottom of each of the insertion grooves 44. The electrical actuators 46, are configured to include a housing 46a buried in the casing 42, and a drive rod 46b, disposed housed within the housing 46a. The drive rod 46b is coupled to a feed screw mechanism formed from a screw spindle and drive nut, and the screw spindle is also connected to a motor through a worm wheel and a worm gear. The electrical actuator 46 configured in this manner extends and retracts in the axial direction of the drive rod 46b by rotating the screw spindle with rotation of the motor.

Figure 4:
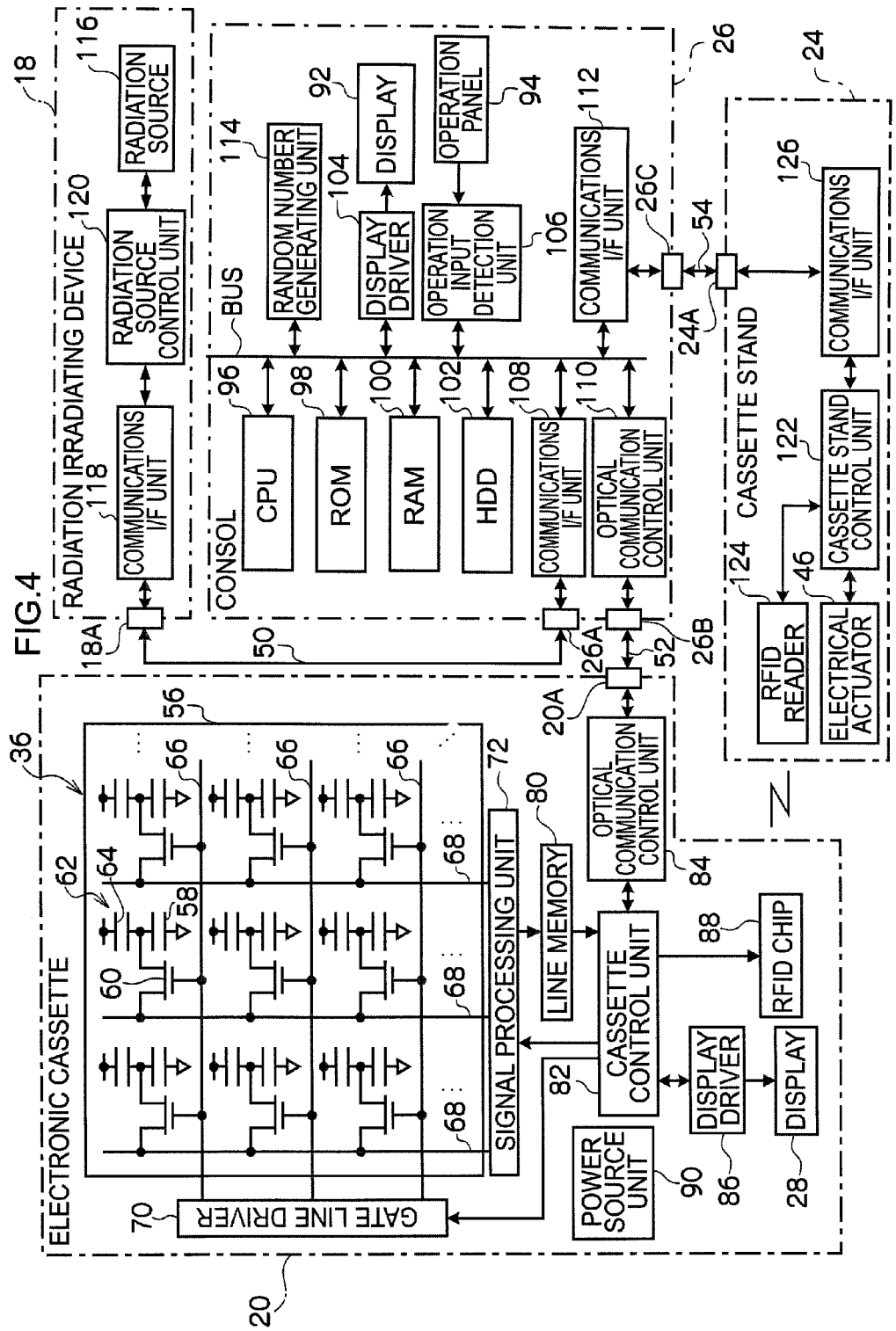
FIG. 4 is a block diagram showing a configuration of an imaging system according to an exemplary embodiment.

FIG. 4 shows a block diagram of a configuration of an imaging system 10 according to the first exemplary embodiment.

A connection terminal 18A is provided to the radiation irradiating device 18 for communicating with the consol 26. The consol 26 is provided with: a connection terminal 26A for communicating with the radiation irradiating device 18; a connection terminal 26B for communicating with the electronic cassette 20; and a connection terminal 26C for communicating with the cassette stand 24. A connection terminal 24A is provided to the cassette stand 24 for communicating with the consol 26.

The radiation irradiating device 18 is connected to the consol 26 through a communications cable 50. When capturing radiographic images a communications cable 52 is connected to the connection terminal 20A, and the electronic cassette 20 is connected to the consol 26 through the communications cable 52. The cassette stand 24 is connected to the consol 26 through a communications cable 54. Note that in the present exemplary embodiment, in order to achieve increased speeds of data transfer between the electronic cassette 20 and the consol 26, an optical communications cable employing an optical fiber is used for the communications cable 52, and data transfer between the electronic cassette 20 and the consol 26 is performed by optical communication.

The radiation detection component 36 installed in the electronic cassette 20 is configured with a photoelectric conversion layer layered on a TFT active matrix substrate 56, for absorbing and converting X-rays into charge. The photoelectric conversion layer is, for example, formed from a-Se (amorphous selenium), with selenium as the main component (for example 50% or more thereof). Charge (electron-hole pairs) are generated within the photoelectric conversion layer when X-rays are irradiated thereon, the charge being of an amount corresponding to the amount of radiation irradiated, thereby converting the irradiated X-rays into charge. Note that in place of the direct radiation-charge converting material such as amorphous selenium that directly converts X-rays into charge, a photoluminescent material and photoelectric conversion element (photodiode) may be employed in the radiation detection component 36, for indirect conversion to charge. Gadolinium oxysulfide compounds (GOS) and cesium iodide (CsI) are well known as photoluminescent materials. In such cases X-ray-light conversion is performed by the photoluminescent material and photon-charge conversion is performed using a photodiode photoelectric conversion element.

Plural individual pixel portions 62 are disposed in a matrix shape on the TFT active matrix substrate 56. Each of the pixel portions 62 is provided with an accumulation capacitor 58, for accumulating the charge generated in the photoelectric conversion layer, and a TFT 60, for reading out the charge that has been accumulated in the accumulation capacitor 58 (in FIG. 4 the photoelectric conversion layer corresponding to each of the pixel portions 62 is shown schematically as a photoelectric conversion portion 64). The charge generated in the photoelectric conversion layer due to irradiation of X-rays onto the electronic cassette 20 is accumulated in the accumulation capacitor 58 of each of the respective pixel portions 62. The image information carried by the X-rays irradiated onto the electronic cassette 20 is thereby converted into the digital data and held in the radiation detection component 36.

Plural gate lines 66 are provided to the TFT active matrix substrate 56 extending in one direction (the row direction), for switching the TFT 60 of the respective pixel portions 62 on and off, and plural data lines 68 are provided, extending in a direction (the column direction) orthogonal to the gate lines 66, through which charge accumulated in the accumulation capacitors 58 is read out through the TFT's 60 that have been switched on. The individual gate lines 66 are connected to a gate line driver 70, and individual data lines 68 are connected to a signal processing unit 72. When charge has been accumulated in the accumulation capacitor 58 of the individual pixel portions 62, the TFT's 60 of the individual pixel portions 62 are switched on in sequence by units of single rows by signals supplied from the gate line driver 70 through the gate lines 66. The data lines 68 transmit charge that has been accumulated in the accumulation capacitors 58 of the pixel portions 62 with switched on TFT's 60 as a charge signal and input the charge signal to the signal processing unit 72. The charge that has been accumulated in the accumulation capacitors 58 of the pixel portions 62 is thereby read out in sequence by units of single rows.

Figure 5:
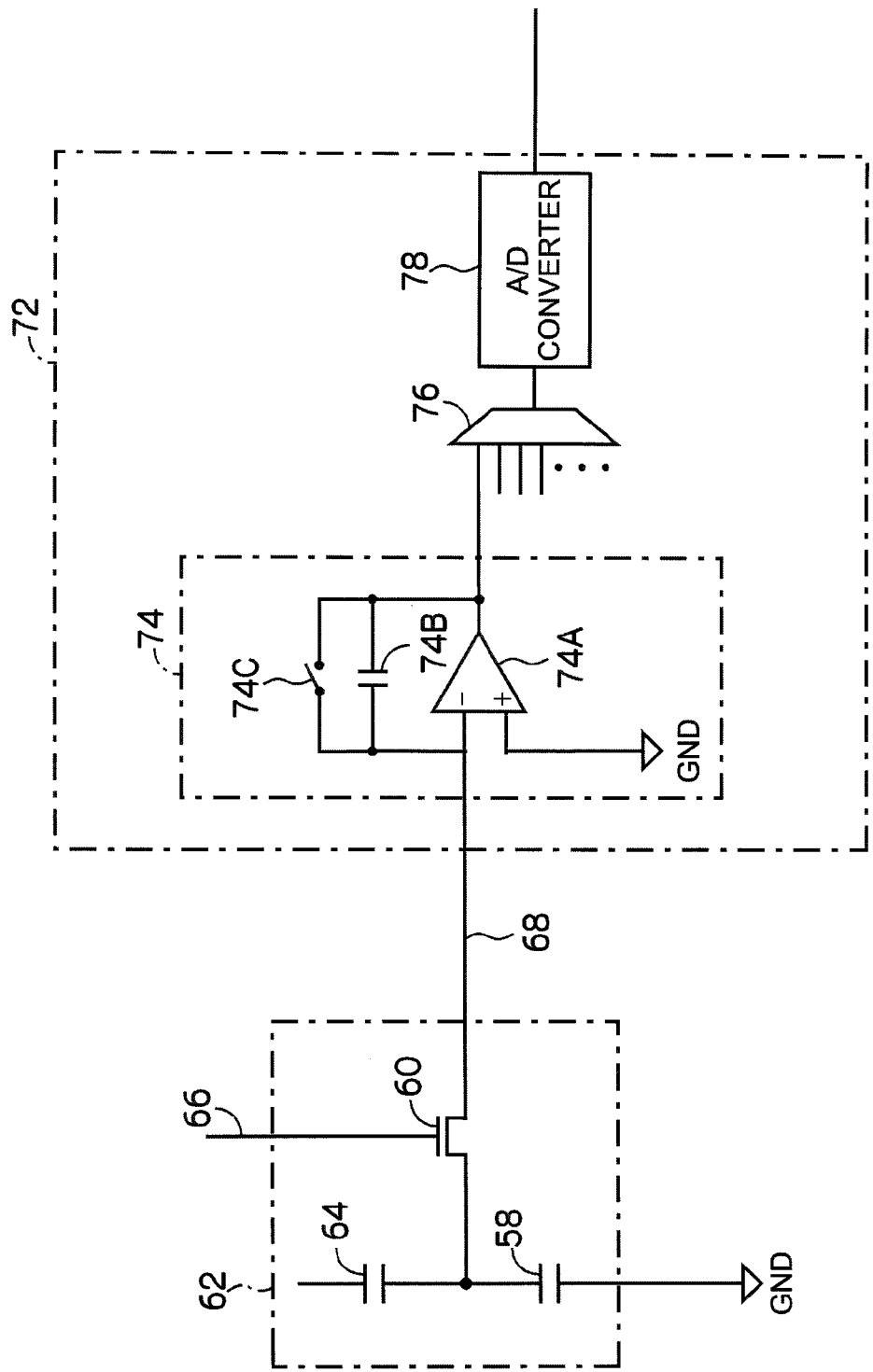
FIG. 5 is an equivalent circuit diagram, focusing on a single pixel portion of a radiation detector according to an exemplary embodiment.

FIG. 5 shows an equivalent circuit diagram, focusing on a single pixel portion of the radiation detection component 36 according to the first exemplary embodiment.

As shown in FIG. 5, the source of the TFT 60 is connected to the data line 68, and this data line 68 is connected to the signal processing unit 72. The drain of the TFT 60 is connected to the accumulation capacitor 58 and to the photoelectric conversion portion 64, and the gate of the TFT 60 is connected to the gate line 66.

The signal processing unit 72 is provided with a sample and hold circuit 74 for each of the data lines 68. The charge signal transmitted by the individual data lines 68 is held in the sample and hold circuits 74. The sample and hold circuits 74 are configured including an operational amplifier 74A and a capacitor 74B, and convert the charge signal into an analogue voltage. A switch 74C is provided in the sample and hold circuit 74 as a reset circuit for shorting both electrodes of the capacitor 74B and discharging the charge that has been accumulated in the capacitor 74B.

The output side of each of the sample and hold circuits 74 is connected in sequence to a multiplexer 76 and an A/D converter 78, and charge signals held in the respective sample and hold circuits 74 are converted into analogue voltages and input in sequence (serially) into the multiplexer 76, and then converted into digital image data by the A/D converter 78.

A line memory 80 is connected to the signal processing unit 72 (see FIG. 4), and the image data output from the A/D converter 78 of the signal processing unit 72 is stored in sequence in the line memory 80. The line memory 80 has sufficient storage capacity capable of storing a specific number of lines worth of image data representing a radiographic image, and each time a single line of charge is read out in sequence, one line's worth of the image data is stored in sequence in the line memory 80.

The line memory 80 is connected to a cassette control unit 82 that controls the overall operation of the electronic cassette 20. The cassette control unit 82 is realized by a microcomputer and is connected to the optical communication control unit 84. The optical communication control unit 84 is connected to the connection terminal 20A and controls the transmission of various data between the cassette control unit 82 and external devices through the connection terminal 20A. The cassette control unit 82 is capable of transmitting and receiving various data with external devices through the optical communication control unit 84.

The electronic cassette 20 is provided with a display driver 86 that controls display on the display 28, and the cassette control unit 82 is connected to the display driver 86. The cassette control unit 82 reads out image data stored in the line memory 80 and displays a radiographic image represented by this image data on the display 28.

The electronic cassette 20 is provided with a later described RFID reader 124 and a RFID chip 88 configuring an RFID system (Radio Frequency Identification System; electromagnetic wave identification system). The cassette control unit 82 is connected to the RFID chip 88. An ID number of the electronic cassette 20 is stored in advance in a memory of the RFID chip 88.

The electronic cassette 20 is also provided with a power source unit 90, and the various circuits and elements described above (microcomputer functioning as the gate line driver 70, the signal processing unit 72, the line memory 80, the optical communication control unit 84 and the cassette control unit 82) are operated by electrical power supplied from the power source unit 90. The power source unit 90 has an inbuilt battery (rechargeable battery capable of being recharged) so that the portability of the electronic cassette 20 is not compromised, and the charged battery supplies electrical power to each of the circuits and elements.

The consol 26 is configured with a server computer, and is configured with a display 92 that displays an operation menu, captured radiographic images, etc., and an operation panel 94, configured to include plural keys and through which various data and operation instructions are input (see also FIG. 1).

The consol 26 is provided with: a CPU (Central Processing Unit) 96 that operates the device as a whole; a ROM (Read Only Memory) 98 in which various programs and the like are stored in advance, including a control program; a RAM (Random Access Memory) 100 that temporarily stores various data; a HDD (Hard Disk Drive) 102 that stores and holds various data; a display driver 104 that controls the display of various information on the display 92; an operation input detection unit 106 that detects the state of operation of the operation panel 94; a communications interface (I/F) unit 108 that performs transmission and reception of various data, such as the radiation exposure conditions and information about the state of the radiation irradiating device 18, to and from the radiation irradiating device 18 through the connection terminal 26A and the communications cable 50; an optical communication control unit 110 that is connected to the connection terminal 26B and performs transmission and reception of various data, such as image data, to and from the electronic cassette 20 through the connection terminal 26B and the communications cable 52; a communications I/F unit 112 that is connected to the connection terminal 26C and performs transmission and reception of various data to and from the cassette stand 24 through the connection terminal 26C and the communications cable 54; and a random number generating unit 114 that generates a random number within a predetermined number range (an integer from 0 to 9999 in the present exemplary embodiment).

The CPU 96, ROM 98, RAM 100, HDD 102, display driver 104, operation input detection unit 106, communications I/F units 108, 112, optical communication control unit 110, and random number generating unit 114 are mutually connected to each other through a system BUS. Consequently the following can be performed: access to the CPU 96, ROM 98, RAM 100, and HDD 102; control of display of various information on the display 92 through the display driver 104; picking up through the operation input detection unit 106 the operated state by a user of the operation panel 94; control of transmission and reception of various information to and from the radiation irradiating device 18 through the communications I/F unit 108; control of transmission and reception of various information to and from the electronic cassette 20 through the optical communication control unit 110; control of transmission and reception of various information to and from the cassette stand 24 through the communications I/F unit 112; instruction of the random number generating unit 114 to generated a random number; and acquisition of random numbers generated by the random number generating unit 114.

The radiation irradiating device 18 is configured including: a radiation source 116 that outputs X-rays; a communications I/F unit 118 that is connected to the connection terminal 18A and transmits and receives various information, such as the radiation exposure conditions and information about the state of the radiation irradiating device 18, to and from the consol 26; and a radiation source control unit 120 that controls the radiation source 116 based on the received radiation exposure conditions. The radiation source control unit 120 is realized by a microcomputer and stores the received radiation exposure conditions, and causes X-rays to be radiated from the radiation source 116 based on the stored radiation exposure conditions.

The cassette stand 24 is configured including, in addition to the electrical actuator 46: a cassette stand control unit 122 that is realized by a microcomputer and controls the overall operation of the cassette stand 24; RFID readers 124 that are provided for each of the insertion grooves 44, the RFID readers 124 transmitting electromagnetic waves of a specific frequency and performing wireless communication with the RFID chip 88 so as to read out and acquire ID number stored in the RFID chip 88; and a communications I/F unit 126 that is connected to the connection terminal 24A and transmits and receives various information to and from the consol 26.

The cassette stand control unit 122 is connected to the electrical actuator 46, the RFID reader 124, and the communications I/F unit 126, and can perform the following: control driving of the electrical actuator 46; control transmission and reception of various information to and from the consol 26 through the communications I/F unit 126; and control the operation of the RFID readers 124.

The electronic cassette 20 according to the first exemplary embodiment executes deterioration degree numericalization processing that numericalizes the degree of deterioration of the radiation detection component 36.

Figure 6:
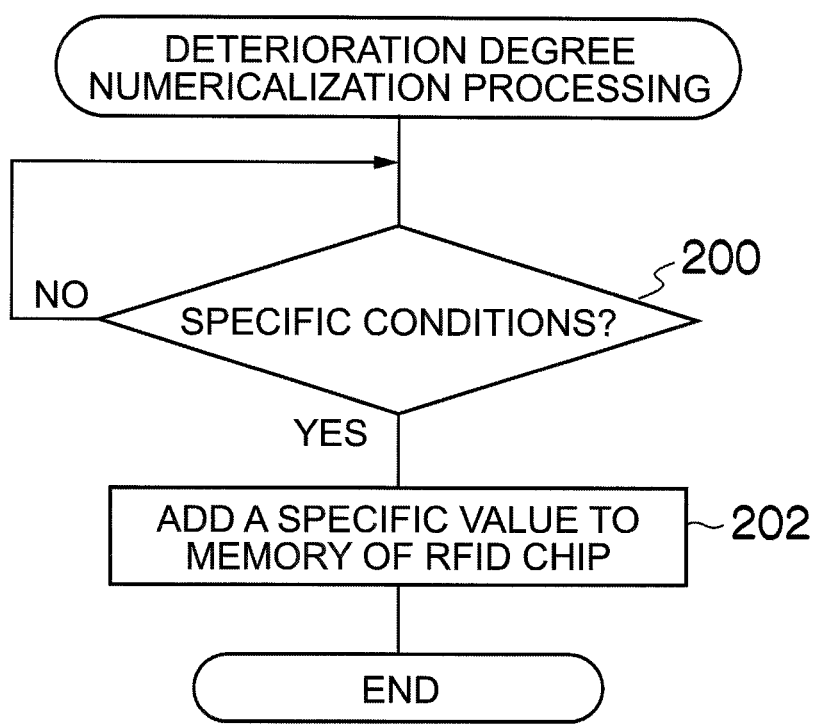
FIG. 6 is a flow chart showing the processing flow in a deterioration degree numericalization processing program according to a first exemplary embodiment.

Explanation will now be given of the processing routine of the electronic cassette 20 when executing the above deterioration degree numericalization processing, with reference to FIG. 6. FIG. 6 is a flow chart showing the processing flow when a deterioration degree numericalization processing program is executed by the cassette control unit 82 of the electronic cassette 20, this program being stored in advance in a specific region of a non-illustrated memory connected to the cassette control unit 82.

The routine is on standby at step 200 in FIG. 6 until an image is captured using the electronic cassette 20, then at the next step 202, "1" is added to the degree of deterioration of the radiation detection component 36 in the specific region of the memory of the RFID chip 88, and the current deterioration degree numericalization processing program is then ended.

In the first exemplary embodiment, the number of times of imaging is counted by adding a degree of deterioration "1" to the specific region of the memory of the RFID chip 88 every time an image is captured using the electronic cassette 20, however there is no limitation thereto. Each time an image is captured using the electronic cassette 20 a value in accordance with the radiation amount detected during image capture may be added as a degree of deterioration to the specific region of the memory of the RFID chip 88. The degree of deterioration is preferably computed from at least one of: the number of times of imaging; the number of defective pixels; the distribution of defective pixels; the cumulative amount of radiation exposure incurred and/or a noise level in the radiation detection component 36. The reliability of the degree of deterioration can thereby be raised.

The number of defective pixels in the radiation detection component 36 increases the greater the number of times of imaging and the greater the amount of radiation irradiated. There is therefore a correlation between the number of defective pixels and the degree of deterioration.

The defective pixels can be detected, for example, by reading out charge that has accumulated in each of the pixel portions 62 of the radiation detection component 36 without irradiation from the radiation irradiating device 18, and by determining whether or not the amount of charge read out is within a normal range for a state in which radiation has not been irradiated.

Even if the number of defective pixels in the radiation detection component 36 is small, the electronic cassette 20 is more deteriorated when the defective pixels are positioned overlapping with the imaging position of the patient 14, due to the greater influence from the defective pixels on the radiographic image.

Figure 11:
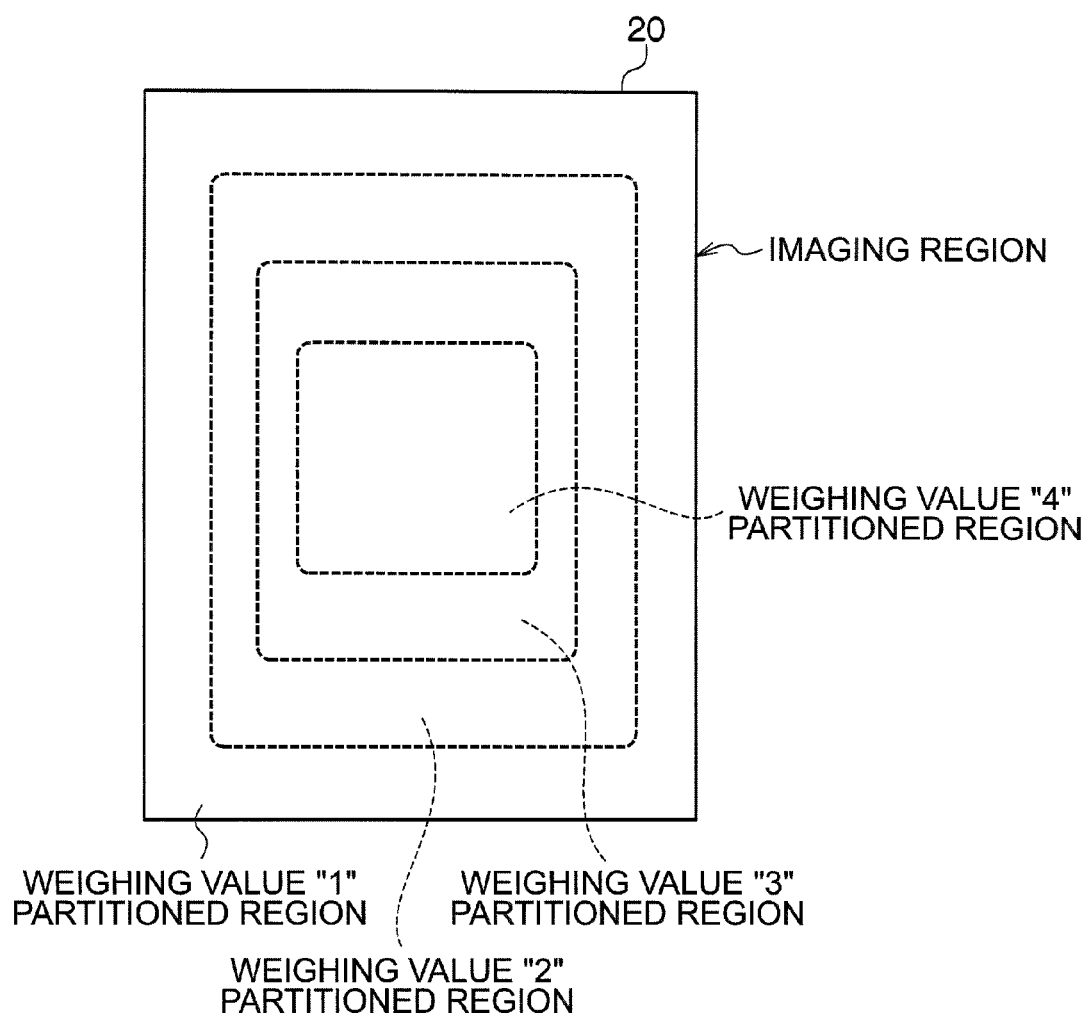
FIG. 11 is a diagram showing an example of an imaging region of a radiation detector according to the first exemplary embodiment that has been divided into partitioned regions.
Figure 12:
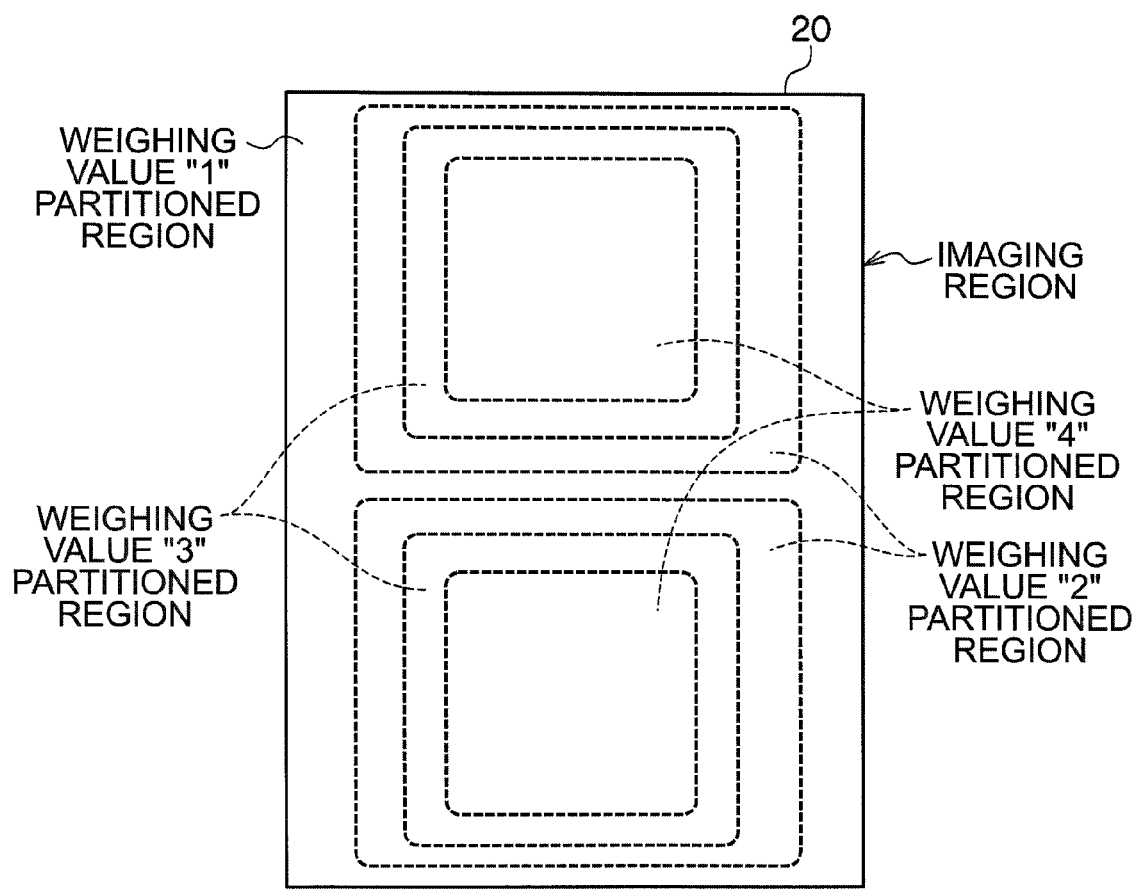
FIG. 12 is a diagram showing another example of an imaging region of a radiation detector according to the first exemplary embodiment that has been divided into partitioned regions.

In order to address this issue the imaging region, capable of imaging a radiographic image, of the radiation detection component 36 may, for example, be partitioned according to the degree of influence on the radiographic image when the defective pixels are positioned therein, and weighing values determined according to the degree of influence for each of the partitioned regions. Then, for each of the partitioned regions, the number of individual defective pixels in the partitioned region is multiplied by the weighing value corresponding to the partitioned region, and the sum of the values obtained by the multiplications for each of the partitioned regions may be used as the degree of deterioration. FIG. 11 and FIG. 12 show examples of weighing values determined for each of the partitioned regions of the imaging region of the radiation detection component 36. In FIG. 11 partitioning is performed such that the weighing values are greater in the vicinity of the center of the imaging region of the radiation detection component 36. However, when the imaging region of the radiation detection component 36 is large, there are occasions where imaging is performed with the imaging position biased toward one or other end in the length direction of the imaging region. In order to address this, in FIG. 12, the imaging region of the radiation detection component 36 is partitioned by splitting in half, such that weighing values are greater in the vicinity of the center in the imaging regions of each half.

Figure 13:
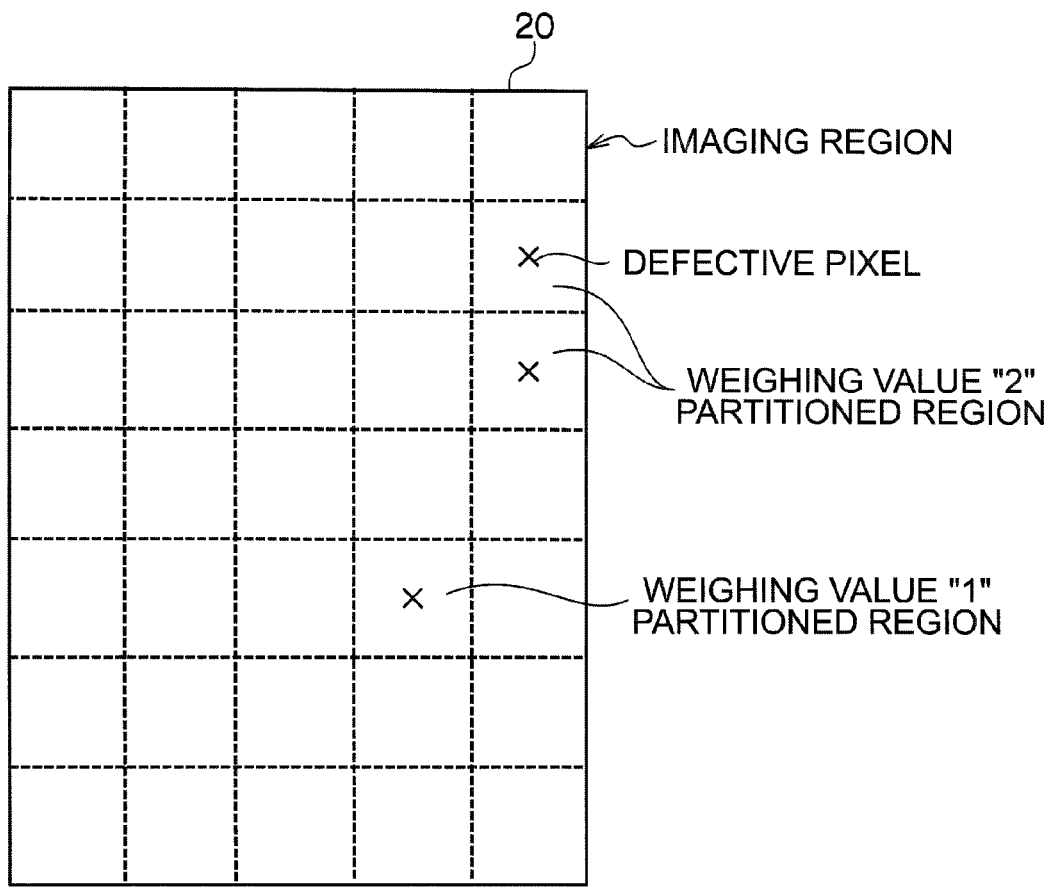
FIG. 13 is a diagram showing an example of an imaging region of a radiation detector according to the first exemplary embodiment that has been divided into matrix shaped partitioned regions.

Also, for example, the imaging region of the radiation detection component 36 may be partitioned into plural equal partitioned regions, with the weighing values changed so as to be increased when adjacent of the partitioned regions have defective pixels, since this has a larger influence on the radiographic image. Then, for each of the partitioned regions, the number of individual defective pixels in the partitioned regions are then multiplied by the weighing values corresponding to the partitioned regions, and the sum of the values obtained by the multiplications for each of the partitioned regions may be used as the degree of deterioration. FIG. 13 shows an example of the imaging region of the radiation detection component 36 split into matrix shaped partitioned regions. For example, as shown in FIG. 13, a weighing value of "1" is applied when there are no defective pixels in the adjacent partitioned regions, and a weighing value of "2" is applied when there are defective pixel(s) in the adjacent partitioned regions.

Noise in the radiation detection component 36 and the sample and hold circuits 74, such as from dark current, increases with deterioration. There is therefore a correlation between the noise level and the degree of deterioration.

By, for example, periodically reading out the charge that has been accumulated in each of the pixel portions 62 of the radiation detection component 36 when not irradiated with radiation from the radiation irradiating device 18, the noise level can be derived from the read out charge amounts. The noise level may, for example, be taken as the increase in the periodically read charge amount with respect to the charge amount read out in the initial period, or the noise level may be taken as the increase in the periodically read charge amount with respect to a specific reference value.

The timing with which the noise level and the defective pixels are detected may, for example, be: once every specific number of times of imaging; when the console 26 is switched ON, and/or when the console 26 is switched OFF; prior to capturing a radiographic image and/or after capturing a radiographic image; at a specific time of day; on a specific date, such as the first day of the month or the last day of the month; or a combination of any of the above.

In the first exemplary embodiment numericalization of the degree of deterioration is performed in the electronic cassette 20, however there is no limitation thereto, and the degree of deterioration may also be performed in the cassette stand 24 or in the consol 26.

When the consol 26 of the first exemplary embodiment is in a state in which plural of the electronic cassettes 20 are accommodated in the cassette stand 24 and a specific input operation is performed to the operation panel 94, the cassette stand control unit 122 is instructed to read out and acquire, using the RFID readers 124, the degree of deterioration and ID numbers stored in the memory of the RFID chip 88 for each of the plural electronic cassettes 20 that are accommodated in the cassette stand 24. The cassette stand control unit 122 associates the read out and acquired degree of deterioration and ID numbers with each other for each of the electronic cassettes 20 and then sends the degree of deterioration and ID numbers to the consol 26. In response to this transmission, the consol 26 executes electronic cassette recommendation processing that recommends particular electronic cassette(s) 20 to be used from the plural electronic cassettes 20 stored in the cassette stand 24.

Figure 7:
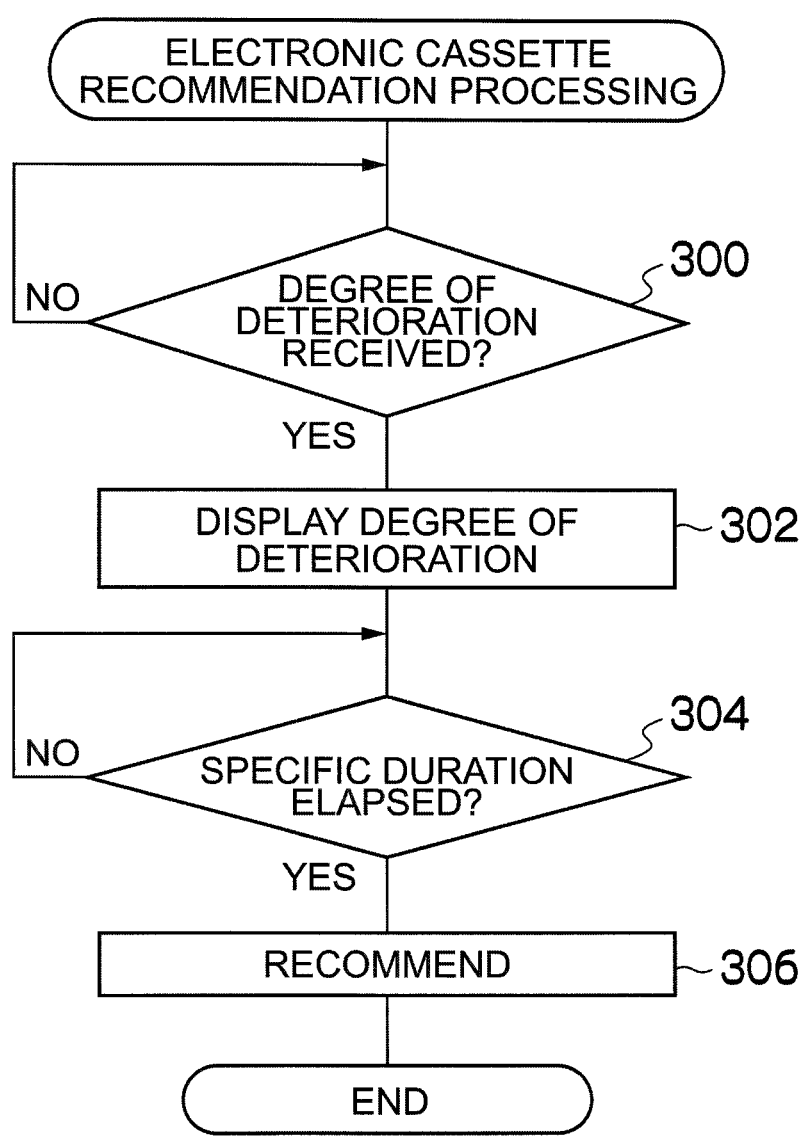
FIG. 7 is a flow chart showing the processing flow in an electronic cassette recommendation processing program according to the first exemplary embodiment.

Explanation will now be given of the processing routine of the consol 26 when the above electronic cassette recommendation processing is executed, as shown in FIG. 7. FIG. 7 is a flow chart showing the processing flow in an electronic cassette recommendation processing program executed in such cases by the CPU 96 of the consol 26, with this program being stored in advance in a specific region of the ROM 98.

The routine is on standby at step 300 in FIG. 7, waiting until receipt of plural sets of ID numbers and degrees of deterioration transmitted from the cassette stand 24, and at step 302 the plural sets of ID numbers and degrees of deterioration received at above step 300 are displayed on the display 92, as in the example thereof shown in FIG. 8. FIG. 8 shows an example of the plural ID numbers and degrees of deterioration.

In the first exemplary embodiment the degree of deterioration is displayed on the display 92 of the consol 26, however there is no limitation thereto, and the degree of deterioration may be displayed on the display 28 of the corresponding electronic cassette 20. In such cases reading out and acquiring the ID numbers and degrees of deterioration using the RFID readers 124 of the cassette stand 24 becomes unnecessary. A display may also be provided to the cassette stand 24, and the degree of deterioration for each of the electronic cassettes 20 read out by the RFID readers 124 and displayed on such a display. In such cases transmitting the ID numbers and degrees of deterioration, read out and acquired using the RFID readers 124 for each of the electronic cassettes 20, becomes unnecessary.

At the next step 304, the routine is on standby until a specific duration (for example 20 seconds) has elapsed since completion of the processing of step 302, and then at the next step 306 a recommendation message recommending the use of the electronic cassette 20 with the ID number corresponding to the greatest degree of deterioration, from the plural degrees of deterioration received in the above step 300, is displayed on the display 92, as in the example thereof shown in FIG. 9. The current electronic cassette recommendation processing program is then ended. FIG. 9 shows an example of the recommendation message displayed on the display 92.

A recommendation message is displayed on the display 92 recommending the use of the electronic cassette 20 of the ID number corresponding to the greatest degree of deterioration in the processing of the above step 306, however there is no limitation thereto. For example, a recommendation message recommending use of the electronic cassette(s) 20 with the ID number corresponding to a degree of deterioration that is of a predetermined threshold value or greater may be displayed on the display 92. An audible notification of the recommendation message may also be made using a voice reproduction device such as a speaker, or a permanent visual display of the recommendation message may be made by printing on recording paper or the like using an image forming apparatus such as a printer. In the processing of above step 306 the recommendation message is displayed on the display 92 of the consol 26, however there is no limitation thereto, and the recommendation message may be displayed on the display 28 of the electronic cassette 20, or a display provided to the cassette stand 24 and the recommendation message displayed thereon.

As explained in detail above, the imaging system 10 of the first exemplary embodiment is provided with: plural of the electronic cassettes 20, each of the electronic cassettes 20 having the radiation detection component 36 that detects the X-rays that have passed through the patient 14, and imaging by generating image data representing a radiographic image according to the amount of radiation detected by the radiation detection component 36, and storing the image data in the line memory 80; and the cassette control unit 82, that numericalizes the degree of deterioration of the radiation detection component 36 for each respective electronic cassette of the plural electronic cassettes 20. The imaging system 10 is thereby able to support concentrated use of particular electronic cassette(s) 20 from the plural electronic cassettes 20.

In the imaging system 10 according to the first exemplary embodiment the degrees of deterioration numericalized by the cassette control unit 82 and associated with the ID numbers of the electronic cassettes 20 are also displayed by means of the display 92, therefore the doctor 12 or radiographer can be readily informed of which electronic cassette 20 it is preferable to use from the plural electronic cassettes 20.

In the imaging system 10 of the first exemplary embodiment the recommendation message recommending the electronic cassette 20 to be used, based on the degree of deterioration numericalized by the cassette control unit 82, is displayed on the display 92, and therefore use of particular electronic cassette(s) 20 can be prompted to a user.

Second Exemplary Embodiment

Explanation has been given in the first exemplary embodiment of an exemplary mode in a case in which recommendation to use the electronic cassette 20 is based on the degree of deterioration, and in the second exemplary embodiment explanation will be given of an exemplary mode in a case where, when imaging plural times, each of the electronic cassettes 20 is selected with a probability according to the degree of deterioration. Note that the configuration of the imaging system according to the second exemplary embodiment is similar to that of the imaging system 10 of the first exemplary embodiment, and explanation thereof will be omitted.

The cassette stand 24 of the imaging system 10 according to the second exemplary embodiment, as explained above in the first exemplary embodiment, reads out and acquires the degree of deterioration and ID numbers from each of the plural electronic cassettes 20 accommodated in the cassette stand 24 when instructed to do so by the consol 26, and transmits the degree of deterioration and ID numbers to the consol 26. In response to this transmission the consol 26 executes electronic cassette selection processing for the cassette stand 24, to select one of the electronic cassettes 20 from the plural electronic cassettes 20 accommodated therein.

Figure 10:
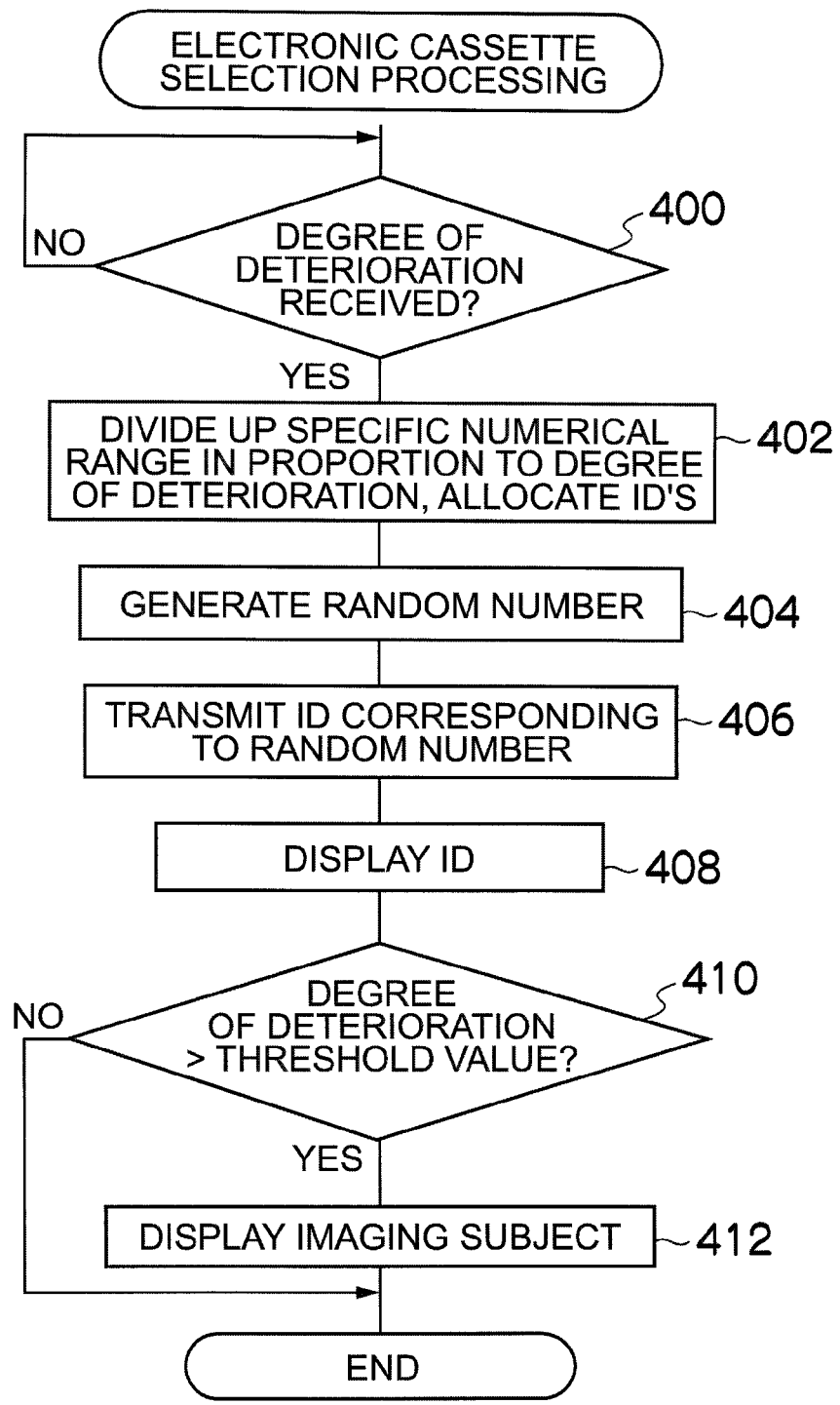
FIG. 10 is flow chart showing the processing flow in an electronic cassette selection processing program according to a second exemplary embodiment.

Explanation will now be given of the processing routine of the consol 26 when executing the above electronic cassette selection processing. FIG. 10 is a flow chart showing the processing flow in an electronic cassette selection processing program when executed by the CPU 96 of the consol 26. This program is stored in advance in a specific region of the ROM 98.

The routine is on standby at step 400 in FIG. 10, waiting for receipt of plural ID numbers and degrees of deterioration to be transmitted from the cassette stand 24, and then at the next step 402, a predetermined numerical range (integers of 0 to 9999 in the second exemplary embodiment) is divided up in proportion to the degrees of deterioration received at above step 400, and the ID numbers associated with their corresponding degrees of deterioration are allocated to the divided numerical range.

For example, in a case in which there is an electronic cassette 20 with applied degree of deterioration "2", an electronic cassette 20 with applied degree of deterioration "3", and an electronic cassette 20 with applied degree of deterioration "5" accommodated in the cassette stand 24, then the integers 0 to 1999 are allocated to the ID number for the degree of deterioration "2", the integers 2000 to 4999 are allocated to the ID number for the degree of deterioration "3", and the integers 5000 to 9999 are allocated to the ID number for the degree of deterioration "5".

In the next step 404, the random number generating unit 114 is instructed to generate a random number. The random number generating unit 114 generates a random number in response to this instruction.

In the next step 406, the ID number allocated to the numerical range, from the plural numerical ranges obtained by dividing in step 402 above, to which the random number, generated by the random number generating unit 114 in the processing of above step 404, belongs is determined, and this ID number is transmitted to the cassette stand 24. In response thereto, the cassette stand control unit 122 of the cassette stand 24 drives the electrical actuator 46 corresponding to the insertion groove 44 accommodating the electronic cassette 20 of the ID number transmitted from the consol 26, so that the drive rod 46b is projected out from the base of the insertion groove 44. A single electronic cassette 20 is thereby pushed out from the insertion groove 44 of the cassette stand 24. The imaging system 10 of the second exemplary embodiment thereby selects the electronic cassette 20 by pushing the electronic cassette 20 out from the cassette stand 24.

In the next step 408, the ID number allocated to the numerical range, from the plural numerical ranges obtained by dividing in step 402 above, to which the random number, generated by the random number generating unit 114 in the processing of above step 404, belongs is displayed on the display 92. The doctor 12 or radiographer can thereby be readily notified of which of the electronic cassette 20 is recommended for use from the plural electronic cassettes 20 accommodated in the cassette stand 24.

In the next step 410, it is determined whether or not the deterioration degree of the electronic cassette 20 corresponding to the ID number allocated to a numerical range to which the random number generated at the random number generating unit 114 by the processing at step 404 exceeds the predetermined threshold. The numerical range to which the random number generated at the random number generating unit 114 is among the numerical ranges obtained by dividing at step 402. When determination is negative then the current electronic cassette selection processing is ended, and when determination is that the threshold value has been exceeded then the routine proceeds to step 412, and after displaying on the display 92 information indicating a predetermined imaging subject, the current electronic cassette selection processing is ended.

Note that for the above predetermined threshold value a value may be applied that is a value obtained in advance such that radiographic images of image quality of a specific level or greater can be obtained, the value determined by computer simulation etc., based on tests of test electronic cassettes 20, the design specification of the electronic cassettes 20 etc.

An example of the "predetermined imaging subject" above is an imaging subject not requiring precision interpretation.

As explained in detail above, the imaging system 10 according to the second exemplary embodiment is provided with the electrical actuator 46 that, when performing image capture plural times, selects each of the electronic cassettes 20 with a probability according to the degree of deterioration. The imaging system 10 is thereby able to support concentrated use of particular electronic cassette(s) 20 from the plural electronic cassettes 20.

In the imaging system 10 according to the present exemplary embodiment, when the degree of deterioration of the electronic cassette 20 selected by the electrical actuator 46 exceeds the predetermined threshold value, information indicating a predetermined imaging subject is displayed on the display 92. Re-imaging due to deterioration in the properties of the electronic cassette 20 can thereby be prevented.

Third Exemplary Embodiment

Explanation will now be given of a third exemplary embodiment. A feature of the third exemplary embodiment is that the degree of deterioration of the electronic cassettes 20 is periodically transmitted to a server computer provided at an external data center, and replacement timing for the electronic cassettes 20 is determined by the sever computer.

Figure 14:
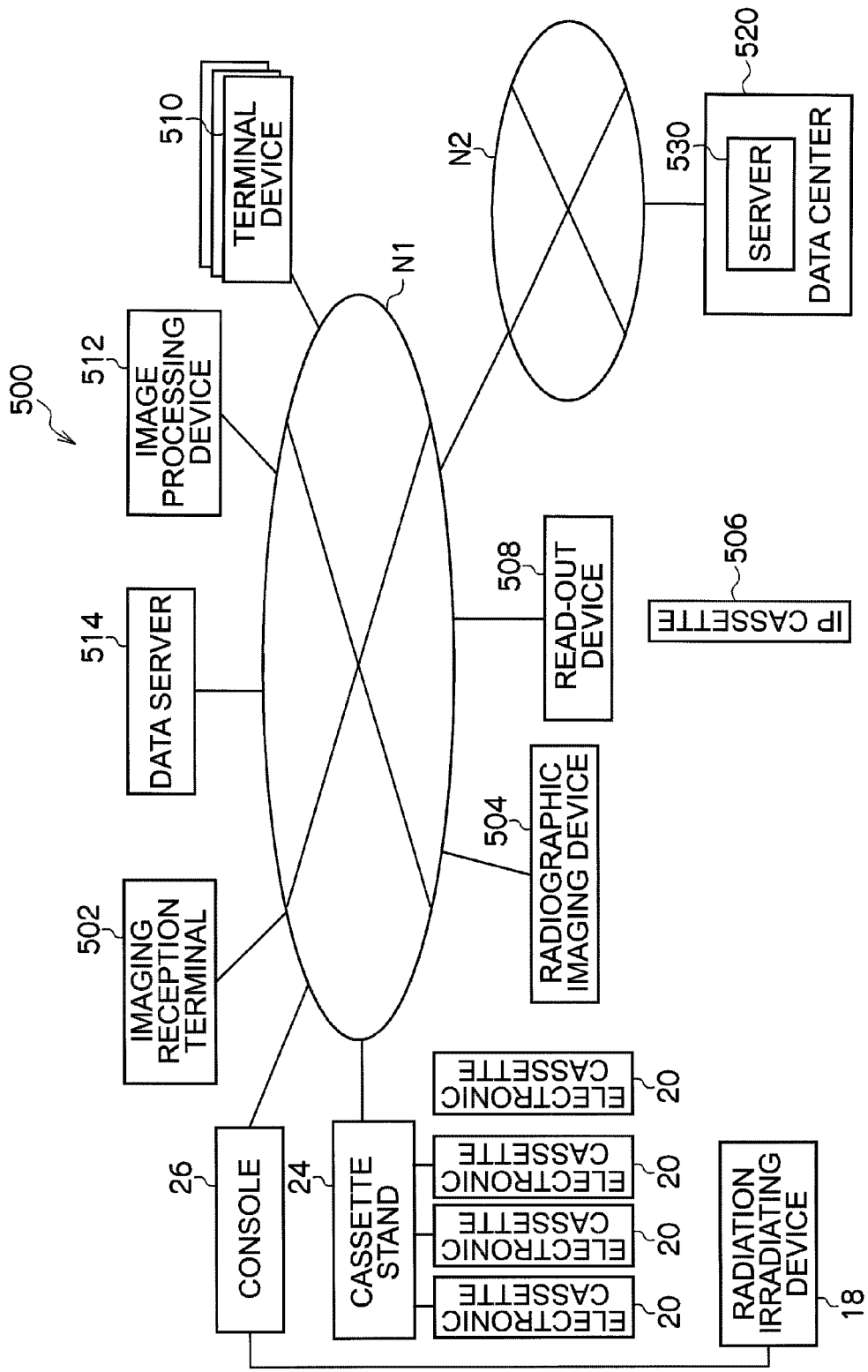
FIG. 14 is a block diagram showing an overall configuration of a Hospital Information System according to a third exemplary embodiment.

FIG. 14 is a block diagram showing an overall schematic configuration of a Hospital Information System (HIS) 500 of a hospital overall, including a radiographic imaging system 10.

The radiographic imaging system 10 according to the third exemplary embodiment configures a portion of the HIS 500, and, in addition to the console 26, the plural electronic cassettes 20, the cassette stand 24 and the radiation irradiating device 18 explained in the above first and second exemplary embodiments, the HIS 500 is also equipped with an imaging reception terminal 502, a fixed radiographic imaging device 504 housing a built-in radiation detection component, an IP cassette 506 with built-in image plate (IP), and a read-out device 508 that reads out a radiographic image from the image plate built into the IP cassette 506.

A console 26, the cassette stand 24, the imaging reception terminal 502, the fixed radiographic imaging device 504 and the read-out device 508 are connected together by a hospital internal network N1 so as to be able to communicate.

There are also plural terminal devices 510, an image processing device 512, and a data server 514 connected to the hospital internal network N1.

The terminal devices 510 are for a doctor or radiographer to input and/or view consultation information and facility appointments, and radiographic image imaging requests (imaging appointments) are also made through the terminal devices 510. Each of the terminal devices 510 are configured by a personal computer with display.

The image processing device 512 is configured by a server computer, and various image processing programs are stored in the image processing device 512, for performing image processing appropriate for interpreting radiographic images and performing image processing for identifying lesions. The image processing device 512 performs various types of image processing on image data representing a radiographic image obtained by image capture.

The data server 514 stores image data representing radiographic images obtained by image capture and image data that has been image processed by the image processing device 512.

The imaging reception terminal 502 is provided at the entrance to the imaging room where radiographic images are captured, and reception processing is performed with the imaging receiver terminal 502 when a doctor or radiographer is capturing radiographic images.

The cassette stand 24 according to the third exemplary embodiment connects the electronic cassettes 20 accommodated therein to the hospital internal network N1 so as enable communication. In FIG. 14 the electronic cassettes 20 accommodated in the cassette stand 24 are connected to the cassette stand 24 by wires. It should be noted that the electronic cassettes 20 may be wireless communication enabled, and wireless communication performed with the console 26 and the hospital internal network N1.

The HIS 500 is also connected to an external network N2, such as the internet, through a networking device such as a router, enabling communication to be performed via the external network N2 with a sever computer (referred to below as "server") 530 provided in a data center 520.

Figure 15:
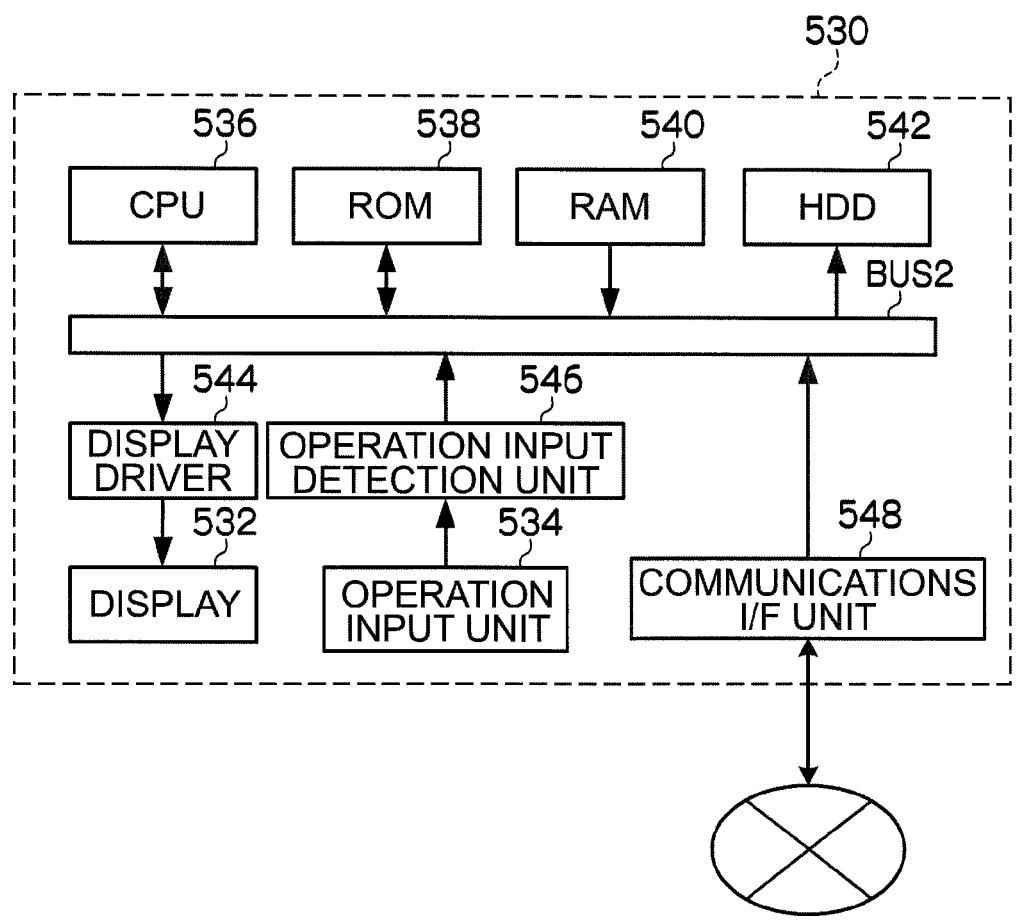
FIG. 15 is a block diagram showing a configuration of a server according to the third exemplary embodiment.

FIG. 15 shows a detailed configuration of a server 530 according to the present exemplary embodiment.

The server 530 is equipped with a display 532 that displays an operation menu, messages etc., and an operation input unit 534, such as a keyboard and pointer device etc., through which various operation instructions are input by a user.

The server 530 is also equipped with: a CPU 536 that controls the operation of the devices overall; a ROM 538, serving as a recording medium, on which various programs and the like, including a control program, are stored in advance; a RAM 540 on which various data is temporarily stored; an HDD 542 on which various data, including installed software, is stored and held; a display driver 544 that controls display of various information on the display 532; an operation input detection unit 546 that detects the operational state of the operation input unit 534; and a communications I/F unit 548 for performing communication with an external network N2.

The CPU 536, the ROM 538, the RAM 540, the HDD 542, the display driver 544, the operation input detection unit 546, and the communications I/F unit 548 are mutually connected to each other via a system BUS 2. Consequently the CPU 536 accesses the ROM 538, the RAM 540, and the HDD 542, controls the display of various information on the display 532 via the display driver 544, and controls transmission and receipt of data to and from the radiation irradiating device 18 via the communications I/F unit 548. The CPU 536 ascertains the operational state of a user toward the operation input unit 534 through the operation input detection unit 546.

The console 26 according to the present exemplary embodiment periodically instructs a cassette stand control unit 122 to read out the degree of deterioration and the ID number from the memory of an RFID chip 88 of the electronic cassettes 20. The cassette stand control unit 122 reads out the degree of deterioration and the ID number stored in the memory of the RFID chip 88 of each of the electronic cassettes 20 accommodated in the cassette stand 24 using an RFID reader 124, and transmits the degrees of deterioration and ID numbers that have been read out to the console 26. The console 26 transmits the read out degree of deterioration and ID number of each of the electronic cassettes 20 as degree of deterioration data to the server 530.

It should be noted that in the third exemplary embodiment numericalization of the degree of deterioration is performed in the electronic cassettes 20 in a similar manner to in the first exemplary embodiment above, however there is no limitation thereto, and numericalization of the degree of deterioration may be performed in the cassette stand 24, the console 26 or the server 530.

The timing with which the console 26 transmits the degree of deterioration data, for example, may be: once every specific number of times of imaging; when the electronic cassette 20 is switched ON, and/or when the electronic cassette 20 is switched OFF; at a specific time of day; on a specific date, such as the first day of the month or the last day of the month; or a combination of any of the above.

On receipt of the degree of deterioration data from the console 26, the server 530 executes replacement timing determination processing that determines the replacement timing for each of the electronic cassettes 20 based on the received degree of deterioration data.

Figure 16:
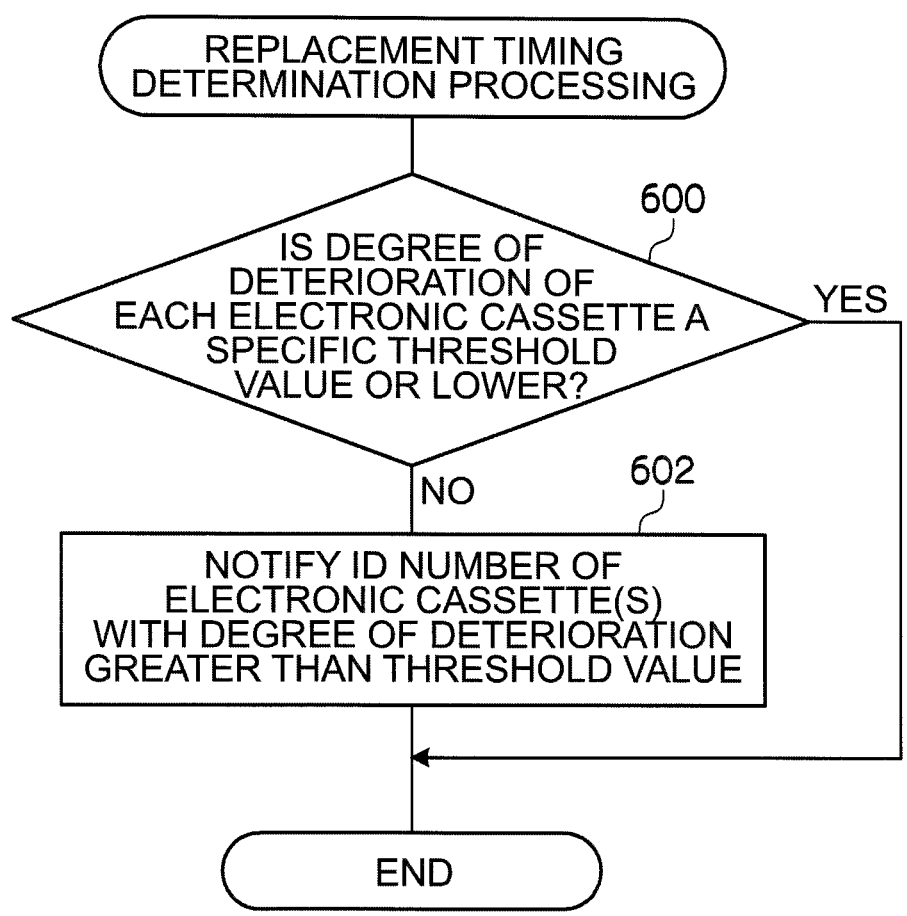
FIG. 16 is a flow chart showing the process flow of a replacement timing determination processing program according to the third exemplary embodiment.

Explanation will now be made of a processing routine in the console 26 when executing the above replacement timing determination processing, with reference to FIG. 16. FIG. 16 is a flow chart showing the process flow in the replacement timing determination processing program executed by the CPU 536 of the server 530 on such occasions, this program being stored in advance in a specific region of the HDD 542.

At step 600 in FIG. 16, determination is made as to whether or not the degree of deterioration of each of the electronic cassettes 20 represented by the degree of deterioration data is of a specific threshold value requiring replacement of the electronic cassette 20, or below that value, and processing is ended when this determination is affirmative, and the routine proceeds to step 602 when the determination is negative.

The above specific threshold value may be derived by tests with the electronic cassettes 20 themselves, or may be derived computer simulation or the like based on the design specification of the electronic cassettes 20 and the like, as long as it is an appropriate threshold value is derived for a degree of deterioration until the image quality of the radiographic images deteriorates to the point at which replacement of the radiation detection component 36 is required.

At step 602, the ID number of any of the electronic cassettes 20 having a degree of deterioration greater than the threshold value is notified to the console 26 via the external network N2 and the hospital internal network N1, and processing is ended.

The console 26 displays a message prompting replacement of the electronic cassettes 20 of the notified ID numbers. Replacement of any of the electronic cassettes 20 with advanced deterioration can thereby be prompted.

When there are any electronic cassettes 20 present with degree of deterioration greater than the threshold value, the server 530 may display the ID numbers of the electronic cassettes 20 having degree of deterioration greater than the threshold value on the display 532, and may dispatch a technician from the data center 520 in order to carry out maintenance or replacement of the electronic cassettes 20.

As explained in detail above, in the server 530 according to the present exemplary embodiment, the degree of deterioration of plural electronic cassettes 20 is acquired through the communications I/F unit 548, and replacement at appropriate timings of the electronic cassettes 20 can be prompted, by the server 530 ascertaining the degree of deterioration of the plural electronic cassettes 20.

The present invention has been explained by way of each of the above exemplary embodiments, however the technical scope of the present invention is not limited to the scope of the exemplary embodiments described above. Various modifications and improvements can be applied to the above exemplary embodiments without departing from the scope of the spirit of the invention, and the technical scope of the present invention also encompasses such modifications and/or improvements.

Each of the above exemplary embodiments does not limit the scope of the invention as recited in the patent claims, and not all of the combinations of features explained within each of the above exemplary embodiments are necessarily essential for the solution of the invention. There are various levels of invention included in each of the above exemplary embodiments, and according to circumstances various inventions can be derived from combinations of the plural configuration conditions disclosed. As long as the effect of the invention can be obtained, even if one or more of the structural conditions are removed from the overall configuration conditions shown in each of the above exemplary embodiments, then the configuration from which one or more of the structural conditions have been removed can also be derived as the invention.

For example, explanation has been given above in the second exemplary embodiment of an example of an exemplary mode in which the electronic cassette 20 is selected from the plural electronic cassettes 20 with a probability according to the degree of deterioration, however the present invention is not limited thereto, and selection may be made by pushing out from the insertion groove 44 of the electrical actuator 46 the electronic cassette(s) 20 from the plural electronic cassettes 20 whose degree of deterioration is of a specific value or greater. Such cases are also able to support concentrated use of particular electronic cassette(s) 20 from the plural electronic cassettes 20. The above specific value may also be varied. Examples of such cases include provision of a mode for resetting the above specific value by inputting the desired value to the operation panel 94, and provision of a multi-level adjustable switch (for example a DIP switch) to the consol 26, with the mode for resetting the above specific value instructed by manipulation of such a switch.

In the second exemplary embodiment above explanation has been given of an exemplary mode in which the electrical actuator 46 is used to push the electronic cassette 20 out from the insertion groove 44, however the invention is not limited thereto, and, for example, a solenoid may be used to push the electronic cassette 20 out from the insertion groove 44. Any type of actuator may be used as long as it is capable of pushing the electronic cassette 20 out from the insertion groove 44.

In the second exemplary embodiment above explanation has been given of an exemplary mode in which the electronic cassette 20 is selected by the electrical actuator 46 pushing the electronic cassette 20 out from the insertion groove 44, however the present invention is not limited thereto. For example, a mode may be configured with a light emitting element such as an LED (light emitting diode) provided to the electronic cassette 20, with the electronic cassette 20 selected by causing the light emitting element to emit light, or a mode may be configured with a buzzer provided to the electronic cassette 20, with the electronic cassette 20 selected by sounding the buzzer.

In the above second exemplary embodiment explanation has been given of an exemplary mode in which information is displayed on the display 92 of the consol 26 indicating a predetermined imaging subject, however the present invention is not limited thereto, and information may be displayed on the display 28 of the electronic cassette 20 indicating a predetermined imaging subject. Or a display may be provided to the cassette stand 24 and information indicating a predetermined imaging subject displayed on such a display. Or a display may be provided other than to the consol 26 or to the cassette stand 24, and information indicating a predetermined imaging subject displayed thereon.

In the above second exemplary embodiment, explanation has been given of an exemplary mode in which information is displayed on the display 92 of the console 26 indicating an imaging subject when the degree of deterioration of the electronic cassette 20 recommended for use exceeds a predetermined threshold value, however the present invention is not limited thereto. The degree of deterioration of the electronic cassettes 20 may be split into ranks of plural levels by comparing the degree of deterioration of the electronic cassettes 20 with each of plural levels of threshold values, information indicating an imaging subject corresponding to the degree of deterioration rank may be displayed. For example, the degree of deterioration of the electronic cassettes 20 may be split into ranks at three levels, for example high, medium, low, and an imaging subject requiring a high level of precision in image interpretation (for example lesions of cancer) displayed when the degree of deterioration is low, an imaging subject not requiring such a level of precision in image interpretation (for example inflamed lesions in pneumonia etc.) displayed when the degree of deterioration is medium, and an imaging subject not requiring precision in image interpretation (for example bone fracture locations) displayed when the degree of deterioration is high.

In the above second exemplary embodiment, a warning may also be displayed when the degree of deterioration of the electronic cassette 20 recommended for use exceeds a predetermined threshold value. Since the deterioration of the electronic cassette 20 is known by a doctor 12 or radiographer this thereby acts as motivation for maintenance of the electronic cassette 20.

In the above first and second exemplary embodiments, the degree of deterioration of the electronic cassette 20 may be linked with the information representing the imaging position of the imaging subject and stored in the memory of the electronic cassette 20 (for example in the memory of the RFID chip 88) or in the HDD 102 of the console 26. Management of whether appropriate imaging for the imaging position has been carried out or not can thereby be achieved.

Image data representing a captured radiographic image may also be associated with the degree of deterioration of the electronic cassette 20 on which the radiographic image was captured, and stored. Such associating with the degree of deterioration and storing includes storing the degree of deterioration in a header, footer, or tag of the image data itself, and also linking the degree of deterioration with the image data and storing. Management of the degree of deterioration of electronic cassette 20 with which the radiographic image has been captured can thereby be achieved, and traceability improved.

In each of the above exemplary embodiments explanation has been given of an exemplary mode in which the degree of deterioration and ID numbers are acquired from the electronic cassettes 20 using an RFID system, however the present invention is not limited thereto and the another mode of non-contact communication, such as optical communication, may be used for acquiring the degree of deterioration and ID numbers from the electronic cassettes 20. There is no limitation to using non-contact communication, and a contact type of communication may also be used for acquiring the degree of deterioration and ID numbers from the electronic cassettes 20 by connecting an IC chip to a dedicated terminal.

In the above third exemplary embodiment the an exemplary mode has been explained in which the degree of deterioration and the ID number of each of the electronic cassettes 20 is transmitted as degree of deterioration information from the console 26 to the server 530, however the present invention is not limited thereto. For example, the degree of deterioration of the radiation detection component built into the fixed radiographic imaging device 504 may be derived, and data representing this degree of deterioration transmitted from the fixed radiographic imaging device 504 to the server 530, either directly or via the console 26. In this manner, maintenance of the fixed radiographic imaging device 504 at appropriate times can be prompted since the server 530 can also ascertain the degree of deterioration of the radiation detection component built into the fixed radiographic imaging device 504.

Obviously the configurations of the imaging system 10 explained in the above exemplary embodiments (see FIG. 1 to FIG. 5) are only examples, and modifications may be made thereto according to the circumstances within a scope not departing from the spirit of the present invention.

The processing flow of the deterioration degree numericalization processing program explained in the first exemplary embodiment above (see FIG. 6), the processing flow of the electronic cassette recommendation processing program explained in the first exemplary embodiment above (see FIG. 7), and obviously the processing flow of the electronic cassette selection processing program explained in the second exemplary embodiment above (see FIG. 10) are also only examples, and redundant steps may be removed, additional steps may be added, and the processing sequence may be changed within a scope not departing from the spirit of the present invention.

According to an aspect of the invention there is provided, a management device including: an acquiring component that acquires correlation information that correlates with a degree of deterioration of a radiation detection component from plural imaging devices, each of the plural imaging devices having a radiation detection component that detects radiation that has passed through respective investigation subjects, and each of the plural portable imaging devices performing image capture by generating image data representing a radiographic image according to the amount of radiation detected by the radiation detection component, and storing the image data in a predetermined storage region; and a numericalization component that numericalizes the degree of deterioration of each of the respective radiation detection components of the plural imaging devices based on the correlation information acquired by the acquiring component.

According to the management device of the first aspect, image capture is performed using plural imaging devices, each of the plural imaging devices having a radiation detection component that detects radiation that has passed through respective investigation subjects, by generating image data representing a radiographic image according to the amount of radiation detected by the radiation detection component, and storing the image data in a predetermined storage region, and, using the acquiring component, the correlation information that correlates with the degree of deterioration of the radiation detection component from the plural imaging devices.

In the present invention the degree of deterioration of each of the respective radiation detection components of the plural imaging devices is also numericalized by the numericalization component.

According to the management device of the present invention, concentrated use on particular imaging devices from the plural imaging devices can thereby be supported, since the degree of deterioration of each of the respective radiation detection components of the plural imaging devices is numericalized.

A second aspect of the present invention is the management device of the first aspect further including a display component that corresponds and displays the degree of deterioration numericalized by the numericalization component against each of the respective imaging devices. A user can thereby be readily informed of which imaging device(s) is/are preferably used from the plural imaging devices.

A third aspect is the management device of the first or second aspects, further including a recommendation component that recommends use of one of more of the imaging devices based on the degree of deterioration numericalized by the numericalization component. Use of particular imaging device(s) can thereby be prompted to a user.

A fourth aspect is the management device of the first or second aspects, further including a selection component that, when imaging plural times, selects each of the imaging devices from the plural imaging devices with a probability according to the degree of deterioration, based on the degree of deterioration numericalized by the numericalization component. Use of imaging device(s) selected from the plural imaging devices with a probability according to the degree of deterioration can thereby be prompted to a user.

A fifth aspect is the management device of the first or second aspects, further including a selection component that selects the imaging device(s) from the plural imaging devices whose degree of deterioration is a specific value or greater. Use of imaging device(s) with a degree of deterioration that is a specific value or greater can thereby be prompted to a user.

A sixth aspect is the management device of the fourth or fifth aspects, further including a display component that displays information representing a predetermined imaging subject when the degree of deterioration of the imaging device selected by the selection component exceeds a threshold value. Re-imaging due to deterioration in the properties of the imaging device can thereby be prevented.

A seventh aspect is the management device of any of the first to the sixth aspects, wherein the correlation information is at least one of the number of times of imaging, the number of defective pixels in the radiation detection component, the distribution of defective pixels in the radiation detection component the cumulative amount of radiation exposure incurred and/or a noise level in the radiation detection component. The reliability of the degree of deterioration of the radiation detection component can thereby be raised.

An eighth aspect of the present invention is a storage medium readable by a computer, the storage medium storing a program of instructions executable by the computer to perform a function of managing imaging devices, the function including: numericalizing the degree of deterioration of each of respective radiation detection components of plural imaging devices, each of the plural imaging devices including one of the radiation detection components that detects radiation that has passed through respective investigation subjects, and each of the plural imaging devices performing image capture by generating image data representing a radiographic image according to the amount of radiation detected by the radiation detection component, and storing the image data in a predetermined storage region.

According to the eighth aspect, concentrated use on particular imaging devices from the plural imaging devices can thereby be supported, in a similar manner to in the first aspect.

According to the eights aspect of the present invention, the effect can be obtained of being able to support concentrated use on particular imaging devices from plural imaging devices.

A ninth aspect of the present invention is an imaging device including: a radiation detection component that detects radiation that has passed through a respective investigation subject; a generation component that generates image data representing a radiographic image according to the amount of radiation that has been detected by the radiation detection component; a storage component that stores the image data that has been generated by the generation component; and a numericalization component that numericalizes a degree of deterioration of the radiation detection component based on correlation information that correlates with the degree of deterioration of the radiation detection component.

According to the ninth aspect of the present invention, the effect can be obtained of being able to support concentrated use on particular imaging devices from plural imaging devices.

An imaging device of exemplary embodiments of the present invention is not limited to any one of a portable imaging device and a fixed imaging device. The imaging device of exemplary embodiments of the present invention may be a portable imaging device, a fixed imaging device, a mixed portable imaging device, or the like.

What is claimed is:

1. A management device comprising:
an acquiring component that acquires correlation information that correlates with a degree of deterioration of a radiation detection component from plurality of imaging devices, each of the plurality of imaging devices comprising a radiation detection component that detects radiation that has passed through respective investigation subjects, and each of the plurality of imaging devices performing image capture by generating image data representing a radiographic image according to the amount of radiation detected by the radiation detection component, and storing the image data in a predetermined storage region;
a numericalization component that numericalizes the degree of deterioration of each of the respective radiation detection components of the plurality of imaging devices based on the correlation information acquired by the acquiring component; and a recommendation component that recommends use of at least one of the imaging devices based on the degree of deterioration numericalized by the numericalization component.

2. The management device of claim 1, wherein the correlation information is at least one of: the number of times of imaging; the number of defective pixels in the radiation detection component; the distribution of defective pixels in the radiation detection component; the cumulative amount of radiation exposure incurred; and a noise level in the radiation detection component.

3. A storage medium readable by a computer, the storage medium storing a program of instructions executable by the computer to perform a function of managing imaging devices, the function comprising:
  numericalizing the degree of deterioration of each of respective radiation detection components of a plurality of imaging devices, each of the plurality of imaging devices comprising one of the radiation detection components that detects radiation that has passed through respective investigation subjects, and each of the plurality of imaging devices performing image capture by generating image data representing a radiographic image according to the amount of radiation detected by the radiation detection component, and storing the image data in a predetermined storage region; and
  recommending use of at least one of the imaging devices based on the numericalized degree of deterioration.

4. A management device comprising:
  an acquiring component that acquires correlation information that correlates with a degree of deterioration of a radiation detection component from plurality of imaging devices, each of the plurality of imaging devices comprising a radiation detection component that detects radiation that has passed through respective investigation subjects, and each of the plurality of imaging devices performing image capture by generating image data representing a radiographic image according to the amount of radiation detected by the radiation detection component, and storing the image data in a predetermined storage region;
  a numericalization component that numericalizes the degree of deterioration of each of the respective radiation detection components of the plurality of imaging devices based on the correlation information acquired by the acquiring component; and
  a selection component that, when imaging a plurality of times, selects each of the imaging devices from the plurality of imaging devices with a probability according to the degree of deterioration, based on the degree of deterioration numericalized by the numericalization component.

5. The management device of claim 4 further comprising a display component that displays information representing a predetermined imaging subject when the degree of deterioration of the imaging device selected by the selection component exceeds a threshold value.

6. The management device of claim 4, wherein the correlation information is at least one of: the number of times of imaging; the number of defective pixels in the radiation detection component; the distribution of defective pixels in the radiation detection component; the cumulative amount of radiation exposure incurred; and a noise level in the radiation detection component.

7. A management device comprising:
  an acquiring component that acquires correlation information that correlates with a degree of deterioration of a radiation detection component from plurality of imaging devices, each of the plurality of imaging devices comprising a radiation detection component that detects radiation that has passed through respective investigation subjects, and each of the plurality of imaging devices performing image capture by generating image data representing a radiographic image according to the amount of radiation detected by the radiation detection component, and storing the image data in a predetermined storage region;
  a numericalization component that numericalizes the degree of deterioration of each of the respective radiation detection components of the plurality of imaging devices based on the correlation information acquired by the acquiring component; and
  a selection component that selects the imaging device(s), from the plurality of imaging devices, whose degree of deterioration is a specific value or greater.

8. The management device of claim 7 further comprising a display component that displays information representing a predetermined imaging subject when the degree of deterioration of the imaging device selected by the selection component exceeds a threshold value.

9. The management device of claim 7, wherein the correlation information is at least one of: the number of times of imaging; the number of defective pixels in the radiation detection component; the distribution of defective pixels in the radiation detection component; the cumulative amount of radiation exposure incurred; and a noise level in the radiation detection component.

10. A storage medium readable by a computer, the storage medium storing a program of instructions executable by the computer to perform a function of managing imaging devices, the function comprising:
  numericalizing the degree of deterioration of each of respective radiation detection components of a plurality of imaging devices, each of the plurality of imaging devices comprising one of the radiation detection components that detects radiation that has passed through respective investigation subjects, and each of the plurality of imaging devices performing image capture by generating image data representing a radiographic image according to the amount of radiation detected by the radiation detection component, and storing the image data in a predetermined storage region;
  wherein the function further comprises, when imaging a plurality of times, selecting each of the imaging devices from the plurality of imaging devices with a probability according to the degree of deterioration, based on the numericalized degree of deterioration.

11. A storage medium readable by a computer, the storage medium storing a program of instructions executable by the computer to perform a function of managing imaging devices, the function comprising:
  numericalizing the degree of deterioration of each of respective radiation detection components of a plurality of imaging devices, each of the plurality of imaging devices comprising one of the radiation detection components that detects radiation that has passed through respective investigation subjects, and each of the plurality of imaging devices performing image capture by generating image data representing a radiographic image according to the amount of radiation detected by the radiation detection component, and storing the image data in a predetermined storage region wherein the function further comprises selecting the imaging device(s), from the plurality of imaging devices, whose degree of deterioration is a specific value or greater.

* * * * *